United States Patent
Opsal

(10) Patent No.: US 6,982,791 B2
(45) Date of Patent: Jan. 3, 2006

(54) SCATTEROMETRY TO SIMULTANEOUSLY MEASURE CRITICAL DIMENSIONS AND FILM PROPERTIES

(75) Inventor: Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 348 days.

(21) Appl. No.: 10/319,189

(22) Filed: Dec. 13, 2002

(65) Prior Publication Data

US 2005/0041250 A1    Feb. 24, 2005

Related U.S. Application Data

(60) Provisional application No. 60/346,265, filed on Dec. 19, 2001.

(51) Int. Cl.
*G01J 4/00* (2006.01)

(52) U.S. Cl. .................................................. 356/369
(58) Field of Classification Search ................ 356/369, 356/364; 250/225
See application file for complete search history.

(56) References Cited

U.S. PATENT DOCUMENTS

| | | | | |
|---|---|---|---|---|
| 4,710,642 A | 12/1987 | McNeil | .................. | 250/571 |
| 4,931,132 A | 6/1990 | Aspnes et al. | .............. | 156/601 |
| 5,164,790 A | 11/1992 | McNeil et al. | .............. | 356/355 |
| 5,241,369 A | 8/1993 | McNeil et al. | .............. | 356/445 |
| 5,596,411 A | 1/1997 | Fanton et al. | ................ | 356/369 |
| 5,607,800 A | 3/1997 | Ziger | .......................... | 430/8 |
| 5,739,909 A | 4/1998 | Blayo et al. | ................ | 356/369 |
| 5,798,837 A | 8/1998 | Aspnes et al. | .............. | 356/369 |
| 5,867,276 A | 2/1999 | McNeil et al. | .............. | 356/445 |
| 5,910,842 A | 6/1999 | Piwonka-Corle et al. | ... | 356/369 |
| 5,963,329 A | 10/1999 | Conrad et al. | .............. | 356/372 |
| 6,320,657 B1 * | 11/2001 | Aspnes et al. | .............. | 356/369 |
| 6,449,043 B2 * | 9/2002 | Aspnes et al. | .............. | 356/369 |
| 6,483,580 B1 | 11/2002 | Xu et al. | ..................... | 356/300 |
| 6,611,330 B2 * | 8/2003 | Lee et al. | .................... | 356/369 |
| 6,804,004 B1 * | 10/2004 | Liphardt et al. | ............ | 356/369 |
| 6,822,738 B1 * | 11/2004 | Johs et al. | ................... | 356/369 |
| 6,831,743 B2 * | 12/2004 | Aspnes et al. | .............. | 356/369 |

OTHER PUBLICATIONS

H-T Huang et al., "Normal Incidence SE/RDS for Critical Dimension Monitoring," *ECS Meeting Abstracts*, V.MA-99-1, Abstract No. 244, 1999, one page in length.

(Continued)

*Primary Examiner*—Layla G. Lauchman
(74) *Attorney, Agent, or Firm*—Stallman & Pollock LLP

(57) ABSTRACT

An ellipsometer includes a light source for generating a probe beam of polychromatic light for interacting with a sample. A polarizer is used to impart a known polarization state to the probe beam and the polarized probe beam is directed against the sample at a shallow angle of incidence. A rotating compensator is used to impart phase retardations to the polarization state of the reflected probe beam. After passing through the compensator, the probe beam passes through a second polarizer (analyzer). After leaving the analyzer, the probe beam is received by a detector. The detector translates the received probe beam into a signal that includes DC, $2\omega$ and $4\omega$ signal components (where $\omega$ is the angular velocity of the rotating compensator). A processor analyzes the signal using the DC, $2\omega$ and $4\omega$ components allowing simultaneous evaluation of both critical dimensions and film parameters.

19 Claims, 2 Drawing Sheets

OTHER PUBLICATIONS

H-T. Huang et al., "Normal-incidence spectroscopic ellipsometry for critical dimension monitoring," *Applied Physics Letters*, vol. 78, No. 25, Jun. 18, 2001, pp. 3983-3985.

D.E. Aspnes et al., "Reflectance-difference spectroscopy system for real-time measurements of crystal growth," *Appl. Phys. Lett.*, vol. 52, No. 12, Mar. 21, 1988, pp. 957-959.

* cited by examiner

SCATTEROMETRY TO SIMULTANEOUSLY MEASURE CRITICAL DIMENSIONS AND FILM PROPERTIES

PRIORITY CLAIM

The present application claims priority to U.S. Provisional Patent Application Ser. No. 60/346,265, filed Dec. 19, 2001, the disclosure of which is incorporated herein by reference.

TECHNICAL FIELD

The subject invention relates to ellipsometry systems used to inspect and analyze semiconductor wafers. In particular, the present invention relates to systems for simultaneously measuring critical dimensions and film properties of subject wafers.

BACKGROUND OF THE INVENTION

As geometries continue to shrink, manufacturers have increasingly turned to optical techniques to perform non-destructive inspection and analysis of semi-conductor wafers. The basis for these techniques is the notion that a subject may be examined by analyzing the reflected energy that results when a probe beam is directed at the subject. Ellipsometry and reflectometry are two examples of commonly used optical techniques. For the specific case of ellipsometry, changes in the polarization state of the probe beam are analyzed. Reflectometry is similar, except that changes in magnitude are analyzed. Scatterometry is a related technique that measures the diffraction (optical scattering) that the subject imparts to the probe beam.

Techniques of this type may be used to analyze a wide range of attributes. This includes film properties such as thickness, crystallinity, composition and refractive index. Typically, measurements of this type are made using reflectometry or ellipsometry as described more fully in U.S. Pat. Nos. 5,910,842 and 5,798,837 both of which are incorporated in this document by reference. Critical dimensions (CD) including line spacing, line width, wall depth, and wall profiles are another type of attributes that may be analyzed. Measurements of this type may be obtained using monochromatic scatterometry as described in U.S. Pat. Nos. 4,710,642 and 5,164,790 (McNeil). Another approach is to use broadband light to perform multiple wavelength spectroscopic reflectometry measurements. Examples of this approach are found in U.S. Pat. No. 5,607,800 (Ziger); U.S. Pat. No. 5,867,276 (McNeil); and U.S. Pat. No. 5,963,329 (Conrad). Still other tools utilize spectroscopic ellipsometric measurement. Examples of such tools can be found in U.S. Pat. No. 5,739,909 (Blayo) and U.S. Pat. No. 6,483,580 (Xu). Each of these patents and publications are incorporated herein by reference.

As shown in FIG. 1, a typical optical metrology tool includes an illumination source that creates a mono or polychromatic probe beam. The probe beam is focused by one or more lenses to create an illumination spot on the surface of the subject under test. A second lens (or lenses) and an aperture image the illumination spot (or a portion of the illumination spot) to a detector. The detector captures (or otherwise processes) the received image. A processor analyzes the data collected by the detector. For operation as an ellipsometer, the optical metrology tool includes a polarizer that imparts a known polarization state to the probe beam. A second polarizer, known as an analyzer is used to determine the polarization state of the probe beam after reflection by the subject.

Over time, as the sizes of the features on semiconductor wafers decreases, there is an increasing need to use smaller and smaller illumination spots. For the reflectometry case, measurement can be effectively recorded when the probe beam is directed normally to the subject (normal incidence). This mitigates the difficulty of producing small spot sizes, since normal incidence inherently minimizes the size of the illumination spot. The ellipsometry case is more difficult because sensitivity to film attributes improves as angle of incidence increases. As a result, measurements of this type are typically made using a relatively high angle of incidence, usually around seventy degrees. This spreads the illumination spot into an ellipse whose major radius is equal to its minor radius multiplied by $1/\cos(\theta)$ (where $\theta$ is the angle of incidence). At seventy degrees, the resulting illumination spot is almost three times as long as it would be at normal incidence.

One approach for performing ellipsometric measurements with small spot sizes was developed by the assignee herein. In these systems, a high numerical aperture lens was used to create a spread of angles of incidence with a generally normal incidence beam. Such a system using broadband light is disclosed in U.S. Pat. No. 5,596,411 (Fanton).

More recently, it has been proposed to operate a spectroscopic ellipsometer in a normal incidence mode to measure critical dimensions. More specifically, while normal incidence ellipsometry is insensitive to general thin film parameters, it had been known for some time that such a configuration could be used measure surface anisotropy. (See, "Reflectance-difference Spectroscopy System for Real-time Measurements of Crystal Growth," Aspnes, et. al., Applied Physics Letters, 52 (12) Mar. 21, 1988, page 957.) By extension, the use of such systems for monitoring critical dimensions has been discussed. (See, "Normal Incidence Spectroscopic Ellipsometry for Critical Dimension Monitoring," Huang, et. al, Applied Physics Letters, 78 (25) Jun. 18, 2001, page 3983.) In the latter article, it was shown that changes in polarization state for a near normal incidence beam can be attributed virtually entirely to the surface structure rather than the underlying thin film layers.

Operation at normal incidence produces the smallest possible spot size and is an effective method for measuring critical dimensions. Unfortunately, in cases where thin film measurements are also required, normal incidence measurement has been less effective. For these reasons, there is a need for metrology systems that can accurately measure both surface structure and the parameters of the thin films underlying the structure. Further, it is important that these measurements be made over a relatively small spot size.

SUMMARY OF THE INVENTION

An aspect of the present invention provides a spectroscopic ellipsometer that can simultaneously measure critical dimensions and film properties. For a representative implementation, the ellipsometer includes an illumination source that creates a polychromatic probe beam. The probe beam is passed through a first polarizer to impart a known polarization state to the probe beam. The polarized probe beam is then directed to reflect from the sample at a shallow angle of incidence.

The reflected probe beam passes through a rotating compensator and a second polarizer (analyzer). The compensator imparts a wavelength dependent phase delay to the reflected probe beam. After leaving the analyzer, the probe beam is received by a detector. The detector translates the received probe beam into a signal that includes DC, $2\omega$ and $4\omega$ signal components (where ω is the angular velocity of the rotating compensator). A processor analyzes the signal using the DC, 2ω and 4ω components.

The shallow angle of incidence gives the ellipsometer 200 a relatively small spot size. At the same time, the use of the DC component allows thin film characteristics to be accurately analyzed.

DETAILED DESCRIPTION OF THE PREFERRED EMBODIMENTS

Figure 1:
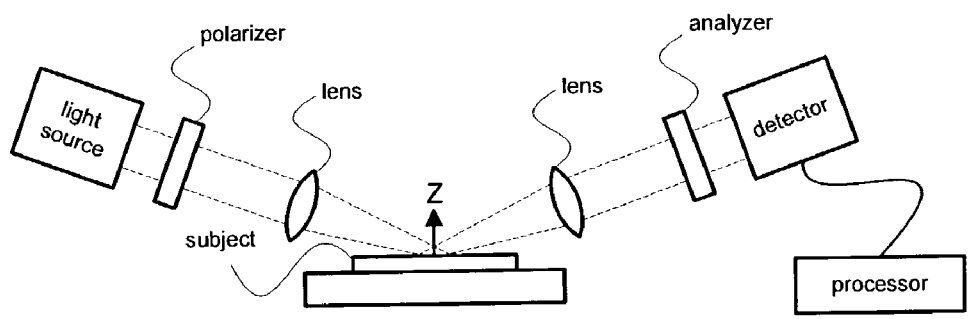
FIG. 1 is a block diagram of prior art optical metrology system.
Figure 2:
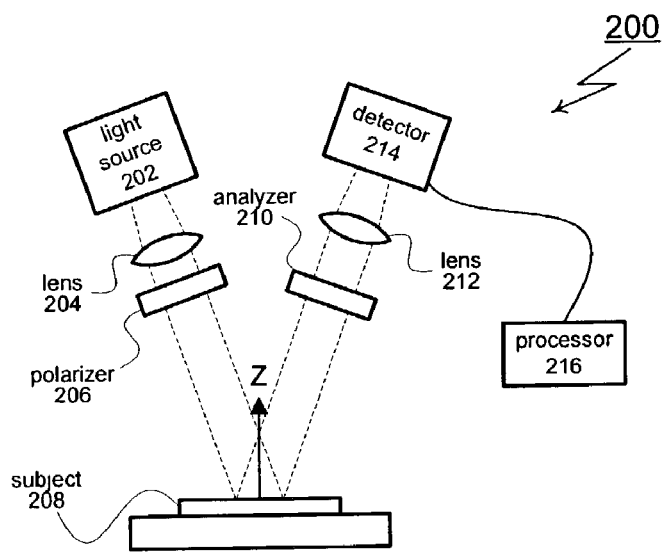
FIG. 2 is a block diagram of an ellipsometer as provided by a first aspect of the present invention.

As shown in FIG. 2, a first aspect of the present invention includes an ellipsometer generally designated 200. Ellipsometer 200 includes an illumination source 202 that creates a mono or polychromatic probe beam. The probe beam is focused by one or more lenses 204 (or other appropriate optical elements such as mirrors) and passed through a polarizer 206. The polarizer 206 imparts a known polarization state to the probe beam. The polarized probe beam creates an illumination spot on the surface of the subject under test 208. An image of the illumination spot (or a portion of the illumination spot) passes through an analyzer 210 and lens 212 before reaching a detector 214. Lens 212 may be selected from a range of different components including achromatic lenses and focusing mirrors. The detector 214 captures (or otherwise processes) the received image. A processor 216 analyzes the data collected by the detector 214.

For the specific example of FIG. 2, the probe beam is directed at an angle of incidence equal ranging from about 20 to 40 degrees. For other embodiments, this angle may range between 10 and 50 degrees. This gives the ellipsometer 200 a relatively small spot size and includes significant off-axis components (i.e., components not directed normally to subject 206) and allows simultaneous evaluation of both critical dimensions and film parameters.

Figure 3:
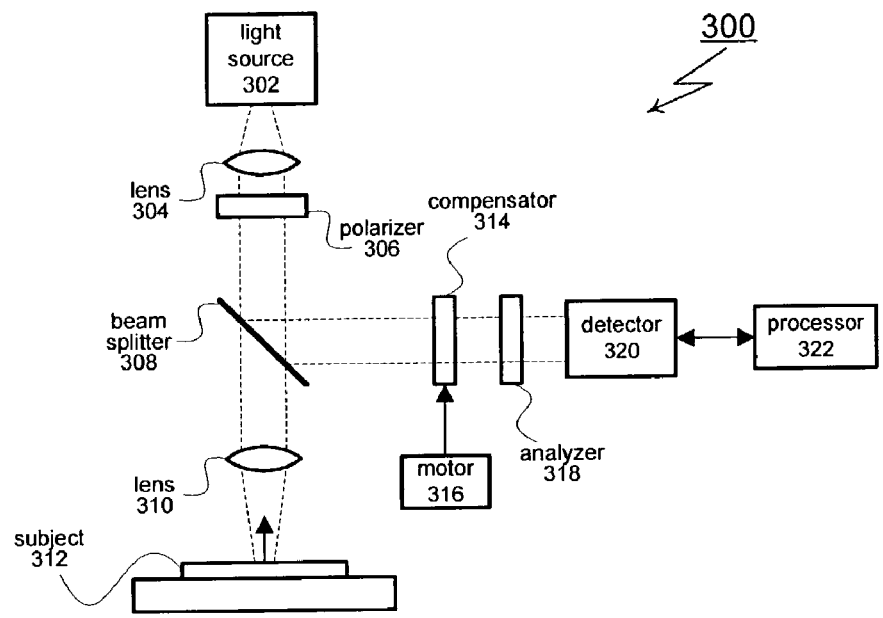
FIG. 3 is a block diagram of an ellipsometer as provided by a second aspect of the present invention.

As shown in FIG. 3, a second aspect of the present invention includes an ellipsometer generally designated 300. Ellipsometer 300 includes a light source 302 that produces a polychromatic probe beam. Light source 302 is typically a Xenon arc lamp and produces a range of wavelengths between 200 to 800 nm. As probe beam leaves light source 302 it is collimated by a lens 304. Lens 304 may be selected from a range of different components including achromatic lenses and focusing mirrors.

After collimation, the probe beam passes though a linear polarizer 306. Linear polarizer 306 imparts a know polarization state to the probe beam. Typically, but not necessarily, the polarization state is complete. Linear polarizer 306 may be omitted if light source 302 emits light having a know polarization state.

The polarized probe beam passes through a beam splitter 308 and is focused by a second lens 310 (or mirror) before reaching a sample 312 to be analyzed. The reflected probe beam passes through the second lens 310 and is redirected by the beam splitter 308. The reflected probe beam then passes through a rotating compensator 314. Compensator 314 introduces a relative phase delay δ (phase retardation) between a pair of mutually orthogonal polarized optical beam components. The amount of phase retardation is a function of wavelength as well as the dispersion characteristics and thickness of the material used to form compensator 314. Compensator 314 is rotated at an angular velocity ω about an axis substantially parallel to the propagation direction of the probe beam. Typically, this is accomplished using an electric motor 316. In general, it may be appreciated that the rotation of the compensator 314 may be continuous or stepped. In cases where the compensator 314 is stepped, a Fourier transformation is used to deduce an effective angular velocity ω.

After leaving compensator 314, the probe beam passes through an analyzer 318. Analyzer 318 is a second linear polarizer preferably oriented at an azimuth angle of 45 degrees relative to the plane of incidence. Interaction with analyzer 318 mixes the polarization state of the probe beam. The probe beam then reaches detector 320. A processor 322 analyzes the data collected by the detector 320.

As it reaches detector 320, the intensity of the probe beam is characterized by the following equation:

$$I[|E_x|^2 + |E_y|^2] = I_0[|E_x|^2 \cos^2(\delta/2) + (1/2)\sin^2(\delta/2) +$$
$$|E_y|^2 (1/2)\sin^2(\delta/2) + (|E_x|^2 - |E_y|^2)(1/2)\sin^2(\delta/2)\cos(4C) +$$
$$\mathrm{Re}(E_x E_y^*)\sin^2(\delta/2)\sin(4C) - \mathrm{Im}(E_x E_y^*)\sin(\delta)\sin(2C)]$$

where $I_o$ is the intensity of the incoming beam, $E_x$ and $E_y$ are the projections of the incident electric field vector parallel and perpendicular, respectively, to the transmission axis of the analyzer, δ is the phase retardation of the compensator, C is the azimuth (rotational) angle of the fast (reference) axis of the compensator also relative to the transmission axis of the analyzer. In the case of a continuously rotating compensator, C=ωt, where ω is the angular rotational frequency of the compensator. As can be seen by the preceding equation, a rotating compensator will generate a signal having a DC component, a 2ω (two omega) component and a 4ω (four omega) component with respect to the rotation rate of the compensator. By measuring the light transmitted by analyzer 318, the polarization state of the reflected probe beam can be determined. A more complete discussion of these components, their characteristics and operation can be found in U.S. Pat. No. 5,877,859 entitled "Broadband Spectroscopic Rotating Compensator Ellipsometer." The disclosure of that patent is included in this document by reference.

To analyze the output of the detector 320, the processor 322 uses the three independent Fourier coefficients (sin 2ω, sin 4ω and cos 4ω) and a suitable fitting algorithm. Preferably, the DC component of the output would be used as well since this component provides additional independent information that can further resolve the thin film analysis. Unlike the Fourier coefficients, the sensitivity of the DC component to changes in film parameters increases as the angle of incidence becomes shallower. Therefore, in a normal incidence embodiment, the DC signal would be the most sensitive to thin film parameters.

Figure 4:
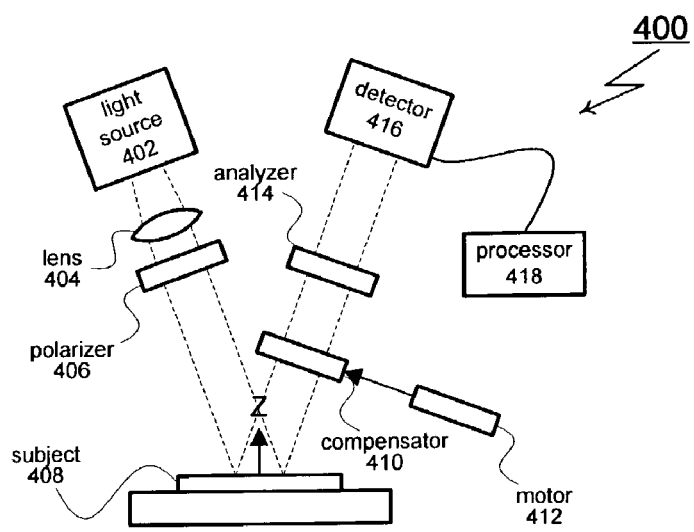
FIG. 4 is a block diagram of an ellipsometer as provided by a third aspect of the present invention.

FIG. 4 shows an ellipsometer 400 according to a third aspect of the present invention. As shown, ellipsometer 400 includes most of the components just described for ellipsometer 300. Ellipsometer 400 is, however, configured to operate at a shallow angle of incidence that is greater than the normal angle of incidence shown for ellipsometer 300. Typical values for the angle of incidence are within the range of 10 to 50 degrees. For this reason, it may be appreciated that ellipsometer 400 is a combination of the two previously described approaches. The shallow angle of incidence of FIG. 2 is used in combination with the rotating compensator of FIG. 3. Ellipsometer 400 is preferably operated using the DC, 2ω and 4ω signal components described for ellipsometer 300.

The use of the shallow angle of incidence (i.e., 10 to 50 degrees) provides a balanced approach that allows critical dimensions as well as thin film properties to be measured simultaneously. At the same time, the illumination spot is maintained at a relatively small size enhancing measurement of wafers that include small geometries.

What is claimed is:

1. An ellipsometric method for evaluating a sample comprising the steps of:
    generating a polychromatic probe beam;
    polarizing the probe beam;
    inducing phase retardations in the polarization state of the probe beam with a compensator, the compensator being substantially non-achromatic so that the amount of phase retardation varies with wavelength;
    directing the probe beam against the sample at an angle of incidence between 10 and 50 degrees;
    rotating the compensator at an effective angular frequency ω;
    passing the probe beam through an analyzer after the probe beam interacts with the sample and with the compensator; and
    measuring the intensity of the probe beam after the interaction with the analyzer at a plurality of wavelengths.

2. A method as recited in claim 1, wherein the intensity of the various wavelengths are measured simultaneously.

3. A method as recited in claim 2, further including the step of angularly dispersing the probe beam after it has interacted with the sample as a function of wavelength.

4. A method as recited in claim 1, further including the step of measuring the intensity of the probe beam before it interacts with the sample and wherein the measurements are used to normalize the measurements made after the probe beam interacts with the sample and the analyzer.

5. A method as recited in 1, wherein the compensator produces a range of retardations that exceeds 180 degrees.

6. A method as recited in claim 1, further including the step of generating an output signal having a DC component, a 2ω component and a 4ω component.

7. A method as recited in claim 6, further including the step of performing a harmonic analysis on the measured output signal to determine normalized Fourier coefficients corresponding to the 2ω and 4ω components.

8. A method as recited in claim 6, further including the step of using the DC, 2ω and 4ω components to simultaneous measure one or more critical dimensions and one or more film properties of the sample.

9. An ellipsometric method for evaluating a sample comprising the steps of:
    generating a polychromatic probe beam;
    polarizing the probe beam;
    directing the probe beam against the sample at an angle of incidence between 10 and 50 degrees;
    passing the probe beam through an analyzer after the probe beam interacts with the sample;
    measuring the intensity of the probe beam after the interaction with the analyzer at a plurality of wavelengths; and
    simultaneously measuring one or more critical dimensions and one or more film properties of the sample.

10. A method as recited in claim 9, wherein the intensity of the various wavelengths are measured simultaneously.

11. A method as recited in claim 11, further including the step of angularly dispersing the probe beam after it has interacted with the sample as a function of wavelength.

12. A method as recited in claim 9, further including the step of measuring the intensity of the probe beam before it interacts with the sample and wherein the measurements are used to normalize the measurements made after the probe beam interacts with the sample and the analyzer.

13. A method as recited in claim 9, further including the step of generating an output signal having a DC component, a 2ω component and a 4ω component.

14. A method as recited in claim 13, further including the step of performing a harmonic analysis on the measured output signal to determine normalized Fourier coefficients corresponding to the 2ω and 4ω components.

15. A method as recited in claim 13, further including the step of using the DC, 2ω and 4ω components to simultaneous measure one or more critical dimensions and one or more film properties of the sample.

16. An ellipsometric apparatus for evaluating a sample comprising:
    a light source for generating a polychromatic probe beam;
    optics for directing the probe beam to interact with the sample at an angle of incidence between 10 and 50 degrees
    a polarizer disposed in the path of the beam;
    a compensator disposed in the path of the light beam, the compensator being substantially non-achromatic so that the amount of phase retardation induced by the compensator varies with wavelength and wherein the compensator rotating with an effective angular frequency ω;
    an analyzer that interacts with the probe beam after the probe beam interacts with the sample and with the compensator;
    a detector for measuring the intensity of the probe beam after the interaction with the analyzer at a plurality of wavelengths; and
    a processor for evaluating the sample based on the measurements made by the detector.

17. An apparatus as recited in claim 16, wherein said probe beam light spans a wavelength range of at least 200 to 800 nm.

18. An apparatus as recited in claim 16, wherein said detector generates output signals which correspond to DC and 2ω and 4ω components and wherein the processor evaluates the sample based on these output signals.

19. An apparatus as recited in claim 16, wherein the optics directs the probe beam to interact with the sample at an angle of incidence between 20 and 40 degrees.

* * * * *